(12) United States Patent
Banta et al.

(10) Patent No.: US 8,415,290 B2
(45) Date of Patent: Apr. 9, 2013

(54) SELF-ASSEMBLING PROTEIN HYDROGEL WITH BIO-ACTIVE PROTEIN

(75) Inventors: Scott Banta, New York, NY (US); Scott Andrew Calabrese Barton, East Lansing, MI (US); Ian R. Wheeldon, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 400 days.

(21) Appl. No.: 12/249,427

(22) Filed: Oct. 10, 2008

(65) Prior Publication Data

US 2009/0075335 A1 Mar. 19, 2009

Related U.S. Application Data

(63) Continuation of application No. PCT/US2007/066454, filed on Apr. 11, 2007.

(60) Provisional application No. 60/791,287, filed on Apr. 11, 2006.

(51) Int. Cl.
| | |
|---|---|
| *A61K 38/00* | (2006.01) |
| *C12N 9/00* | (2006.01) |
| *C07K 1/00* | (2006.01) |
| *C07K 14/00* | (2006.01) |
| *C07K 17/00* | (2006.01) |

(52) U.S. Cl. .......................... 514/1.1; 435/183; 530/350

(58) Field of Classification Search ........................ None
See application file for complete search history.

(56) References Cited

U.S. PATENT DOCUMENTS 5,599,907 A * 2/1997 Anderson et al. ............. 530/385
6,090,911 A 7/2000 Petka et al.

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976) pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Machczynski et al. "Characterization of SLAC: A small laccase from *Streptomyces coelicolor* with unprecedented activity." Protein Science, 2004, vol. 13, pp. 2388-2397.
Kopecek, J. "Smart and genetically engineered biomaterials and drug-delivery systems." European Journal of Pharmaceutical Sciences, 2003, vol. 20, pp. 1-16.
Mi et al, "Self-assembling protein hydrogels with molecular integrin binding domains." Biomacromolecules, 2006, vol. 7, No. 1, pp. 38-47.
ISR and Written Opinion issued on PCT/US07/66454, Jun. 17, 2008.
Mitraki et al., Methods in Molecular Biology, vol. 300: Protein Nanotechnology, Protocols, Instrumentation, and Applications. (2005) 125-140.
Chen, Self-assembly of Ionic-Complementary Peptides: A Physicochemical Viewpoint; Colloids and Surfaces A: Physichochem. Eng. Aspects 261 (2005) 3-24.
Xu, C.; Breedveld, V.; Kopecek, J., Reversible Hydrogels from Self-Assembling Genetically Engineering Protein Block Copolymer. Biomacromol. 2005, 6, 1739-1749.
Pochan, D. J.; Schneider, J. P.; Kretseinger, J.; Ozbas, B.; Rajagopal, K.; Haines, L., Thermally Reversible Hydrogels via Intramolecular Folding and Consequent Self-Assembly of a de Novo Designed Peptide. J. Am. Chem. Soc., 2003, 125, 11802-11803.
Aggeli, A.; Bell, M.; Boden, N.; Keen, J.; Knowles, P. F.; McLeish, T. C. B.; Pitkeathly, M.; Radford, S. E., Responsive gels formed by the spontaneous self-assembly of peptides into polymeric β-sheet tapes. Nature, 1997, 386, 20, 259-262.

* cited by examiner

*Primary Examiner* — Marcela M Cordero Garcia
(74) *Attorney, Agent, or Firm* — Baker Botts, L.L.P.

(57) ABSTRACT

Protein hydrogel monomers incorporating bio-active proteins and methods for producing the same are provided. In some embodiments, the disclosed subject matter includes a protein hydrogel monomer including a bio-active protein and two alpha helices that are adapted to interact with alpha helices on other monomers to form coiled-coil junctions.

20 Claims, 16 Drawing Sheets

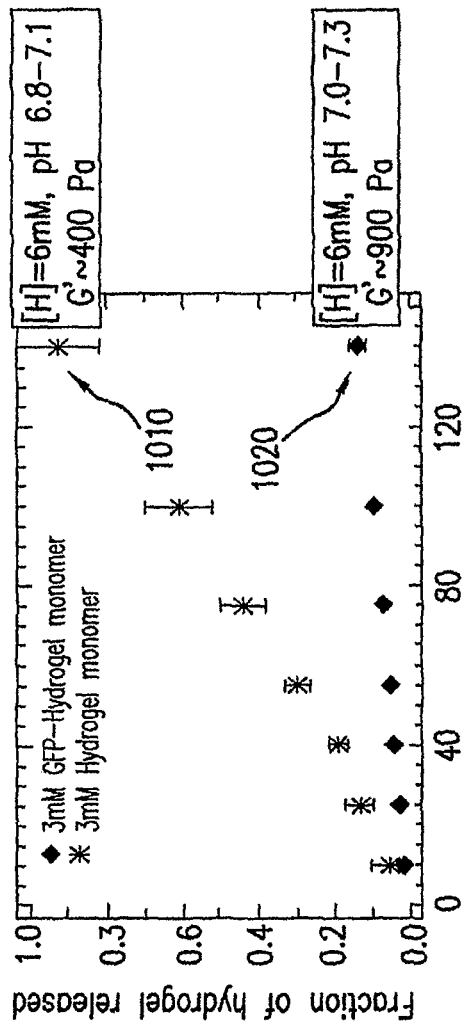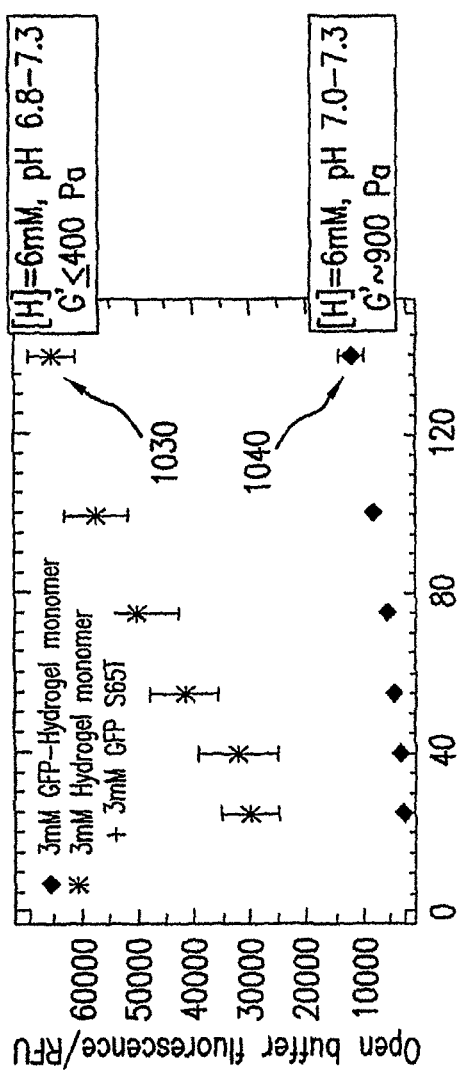
FIG.10A
FIG.10B

Figure 1. Oscillatory shear rheology of 21.1wt% DSRED–Hydrogel monomer at 22°C, with 8mm stainless steel plate geometry, 500μm gap.

SELF-ASSEMBLING PROTEIN HYDROGEL WITH BIO-ACTIVE PROTEIN

CROSS REFERENCE TO RELATED APPLICATION

This application is a continuation of U.S. International Patent Application Ser. No. PCT/US2007/066454, filed on Apr. 11, 2007, which claims priority from U.S. Provisional Patent Application No. 60/791,287, filed Apr. 11, 2006, both of which is are incorporated by reference herein and from which priority is claimed.

STATEMENT REGARDING FEDERALLY SPONSORED RESEARCH

The subject matter described herein was funded in part by a grant from the United States Air Force Office of Scientific Research, MURI Grant No. FA9550-06-1-0264. The United States Government may have certain rights hereunder.

BACKGROUND

1. Technical Field

The disclosed subject matter relates to an improved self-assembling protein hydrogel, and, more specifically, to a self-assembling protein hydrogel that includes a bio-active protein.

2. Background Art

A hydrogel is a two (or more) component three-dimensional network of polymer chains dispersed in water. Hydrogels are very absorbent, and may contain over 99% water. Common uses for hydrogels include use as scaffolding in tissue engineering, as a sustained-release drug delivery system, in contact lenses, in biocatalytic electrodes, and in wound dressings. Common monomers used in hydrogel formation include polyvinyl alcohol, sodium polyacrylate, and other acrylate polymers and copolymers with an abundance of hydrophilic groups.

Hydrogels have become of greater interest recently because they allow enzymes and other bio-active proteins to be immobilized on a surface through entrapment in, or chemical attachment to, a gel matrix. Prior attempts to produce hydrogels incorporating enzymes have attempted to chemically attach enzymes to synthetic polymers or entrap enzymes within a hydrogel. These approaches require a great deal of processing, and correspondingly high costs, while at the same time result in a final product which typically has a non-homogenous distribution of enzyme throughout the gel.

Protein-based hydrogels have received comparatively more attention, as, although they would be less stable and degrade over time, would also be self-assembling (thereby reducing costs).

For example, U.S. Pat. No. 6,090,911 to Petka et al. ("Petka"), the contents of which are herein incorporated by reference, describes a prior-art protein hydrogel monomer. Referring to FIG. 15, the basic building block of the Petka hydrogel is a tri-block polypeptide including a soluble, randomly coiled domain 1510 flanked by two helical domains 1520. The helices are characterized by a heptad repeat of the form abcdefg where a and d are leucine, or non-polar, residues and e and g are charged (both negative and positive) residues.

Referring to FIG. 16, the angular orientation of the helical residues is shown. The side chains of the non-polar leucines lie in a plane along the length of a helix; the hydrophobic nature of the plane leads to the formation of coiled coils. At concentrations greater than approximately 1 wt % tetrameric coiled coils form and tend to precipitate while the randomly coiled domain remains soluble and without secondary structure. A hydrogel is formed as the coiled coil junctions form a colloidal dispersion, physically separated by water-soluble randomly coiled chains.

Precipitation of the protein hydrogel occurs at pH less than 5 as the charged residues at positions e 1610 and g 1620 protonate creating a second non-polar plane leading to the formation of higher-ordered oligomeric bundles of coiled coils. In addition, at pH below 4 the charged residues of the soluble region also protonate reducing the proteins hydrophilicity, causing the protein to precipitate from solution. The upper pH bound of gel formation occurs at pH 11-12 (depending on temperature) as the secondary helical structure of the heptads is lost.

The strength of the interactions between helices within a coiled coil can be tailored through modification of the primary structure. The charged residues at e and g form inter-helical salt bridges adding stability to the structure. Replacement of these residues with similarly charged (i.e. residues with equal charge as its inter-helical pair) or un-charged residues can disfavor the formation of coiled coils. Alternatively, additional salt bridges can be formed with the introduction of more oppositely charged residues. The temperature dependency of the upper pH bound of gel formation is related to the state of deprotonation of the positively charged residues within the helix as the ionic interactions stabilizing the structure are reduced at increasing pH. The fewer salt bridges formed, the less thermal energy is required to denature the helix. At pH 11 α-helical secondary structure is lost at temperatures above 30° C. Under acidic conditions (pH>6) α-helical secondary structure persist at temperatures greater than 80° C.

Although Petka describes a protein hydrogel, the hydrogel incorporates no functional bio-active proteins. Insertion of a bio-active peptide sequence into the hydrogel of Petka has also been described, but incorporation of functional bio-active proteins has not yet been described. (See Mi, L.; Fischer, S.; Chung, B.; Sundelacruz, S.; Harden, J. L., Self-Assembling Protein Hydrogels with Modular Integrin Binding Domains. *Biomacromol.* 2006, 7, 38-47). Accordingly, there exists a need for a protein hydrogel incorporating a bio-active protein which retains its functionality after gel formation and a technique for producing the same.

SUMMARY

Protein hydrogel monomers incorporating bio-active proteins and methods for producing same are disclosed herein. In some embodiments, the disclosed subject matter includes a monomer which includes a bio-active protein, a water-soluble random coil block, and protein blocks on either end of the monomer having structures that can interact with other monomers to form a hydrogel. In some embodiments, the protein blocks are alpha-helices and can interact with alpha-helicies on other monomers to form coiled-coils. In some embodiments, the monomer is symmetrical and includes two water-soluble random coil blocks, one on either side of the bio-active protein.

In other embodiments of the disclosed subject matter, the protein hydrogel monomer includes only one protein block having a structure that can interact with other monomers to form a hydrogel. In some embodiments, the monomer may react with itself to form a multimer, which may then form a hydrogel.

In some embodiments, the disclosed subject matter includes a method of preparing a protein hydrogel monomer which incorporates a bio-active protein. The method includes inserting an expression vector containing hydrogel-forming and bio-active protein domains into a host microorganism. The expression vector causes the expression of the hydrogel-forming and bio-active protein domains as a single protein hydrogel monomer incorporating a bio-active protein. The host is cultured in a growth medium, and the expression of the expression vector is stimulated. The cells are lysed to release the monomer, and the monomer is purified from the lysate.

In some embodiments of the method, the host microorganism used is *E. coli*. Additionally, in some embodiments, purifying the monomer from the lysate includes treating the lysate using nickel affinity chromatography to produce an eluent, conducting buffer exchange on the eluent, and filtering the buffered eluent.

The accompanying drawings, which are incorporated and constitute part of this disclosure, illustrate preferred embodiments of the invention and serve to explain the principles of the disclosed subject matter.

BRIEF DESCRIPTION OF THE DRAWINGS

FIG. 10A is a plot of the fraction of hydrogel released versus time for a hydrogel formed from the prior art monomer and for a hydrogel formed from the GFP monomer produced in accordance with some embodiments of the disclosed subject matter;

FIG. 10B is a plot of the amount of fluorescence in open buffer (as opposed to in the hydrogel) versus time are shown for a hydrogel formed from a mixture of the prior art monomer and unmodified GFP and a hydrogel formed from the GFP monomer produced in accordance with some embodiments of the disclosed subject matter;

Figure 1:
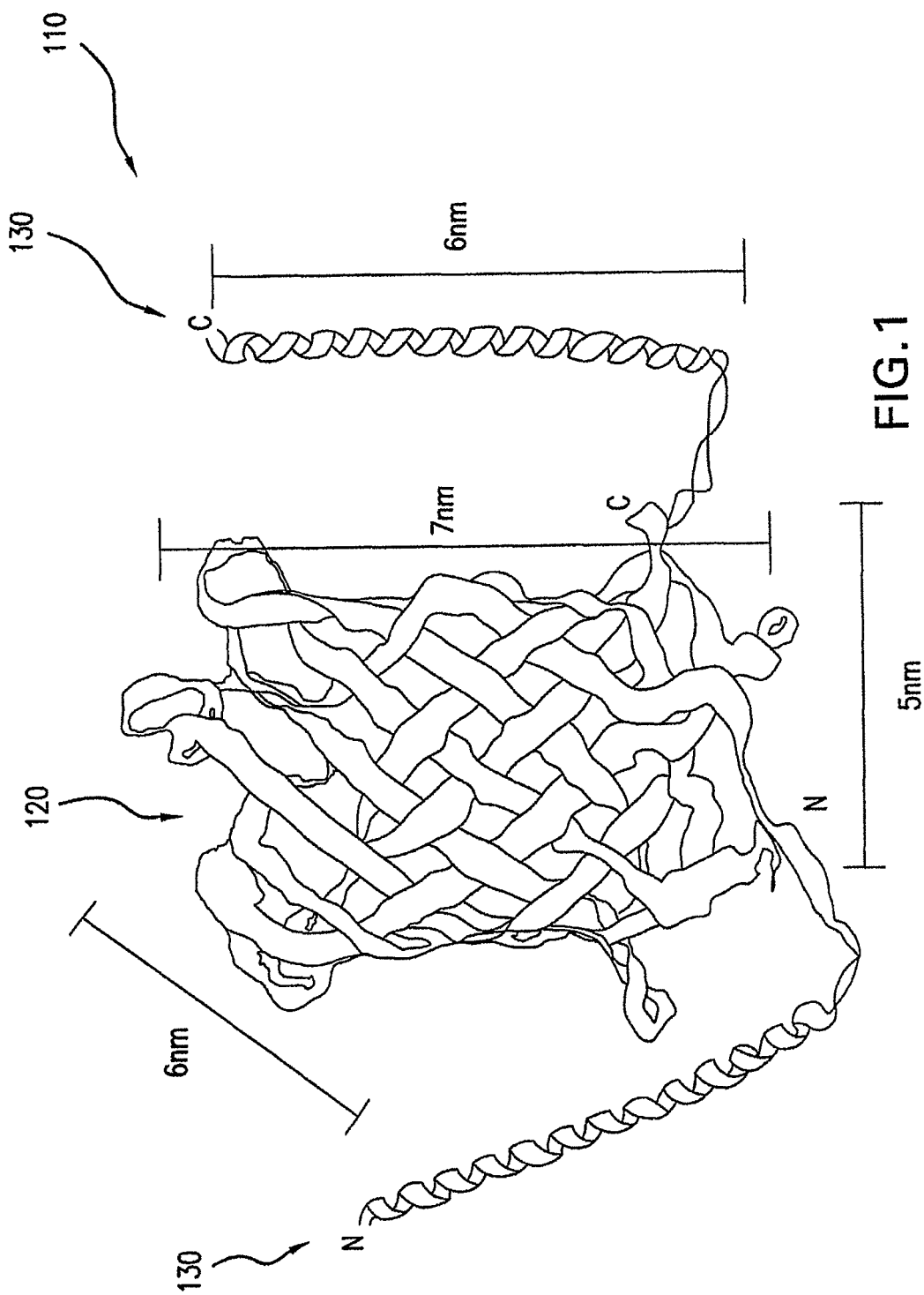
FIG. 1 is a diagram of a protein hydrogel monomer which incorporates a bio-active protein in accordance with some embodiments of the disclosed subject matter.

Throughout the drawings, the same reference numerals and characters, unless otherwise stated, are used to denote like features, elements, components or portions of the illustrated embodiments. Moreover, while disclosed subject matter will now be described in detail with reference to the Figs., it is done so in connection with the illustrative embodiments.

DETAILED DESCRIPTION

The disclosed subject matter relates to protein hydrogel monomers which incorporate bio-active proteins are disclosed. Under certain conditions, the monomers interact with each other to form a hydrogel. The resulting hydrogel incorporates the bio-active proteins and retains the functionality of the bio-active proteins. The disclosed subject matter also includes a method of producing the protein hydrogel monomers using biological manufacturing, in which a host microorganism, such as *E. coli*, is used to produce the monomer as a single protein.

Referring to FIG. 1, a protein hydrogel monomer which incorporates a bio-active protein is presented in accordance with an embodiment of the disclosed subject matter. The monomer 110, which is further described below with regard to FIG. 3, includes a bio-active protein 120 where the bio-active protein termini are functionalized with helices of a peptide hydrogel monomer 130. The bio-active protein 120 is green fluorescent protein (GFP), which is further described in connection with FIG. 4 below. Although the bio-active protein shown in FIG. 1 is GFP other bio-active proteins, such as the DsRed fluorescent protein (DsRed), or enzymes, such as a small laccase (SLAC) provided that the bio-active protein termini are accessible for functionalization, and that such functionalization does not prevent protein function or proper folding. Similarly, other protein-based hydrogel-forming monomers such as those described by Xu et al. (See Xu, C.; Breedveld, V.; Kopecek, J., Reversible Hydrogels from Self-Assembling Genetically Engineering Protein Block Copolymer. *Biomacromol.* 2005, 6, 1739-1749), Pochan et al. (See Pochan, D. J.; Schneider, J. P.; Kretseinger, J.; Ozbas, B.; Rajagopal, K.; Haines, L., Thermally Reversible Hydrogels via Intramolecular Folding and Consequent Self-Assembly of a de Novo Designed Peptide. *J. AM. CHEM. SOC.*, 2003, 125, 11802-11803) and Aggeli et al. (See Aggeli, A.; Bell, M.;

Boden, N.; Keen, J.; Knowles, P. F.; McLeish, T. C. B.; Pitkeathly, M.; Radford, S. E., Responsive gels formed by the spontaneous self-assembly of peptides into polymeric β-sheet tapes. *Nature,* 1997, 386, 20, 259-262) may be used.

Figure 2:
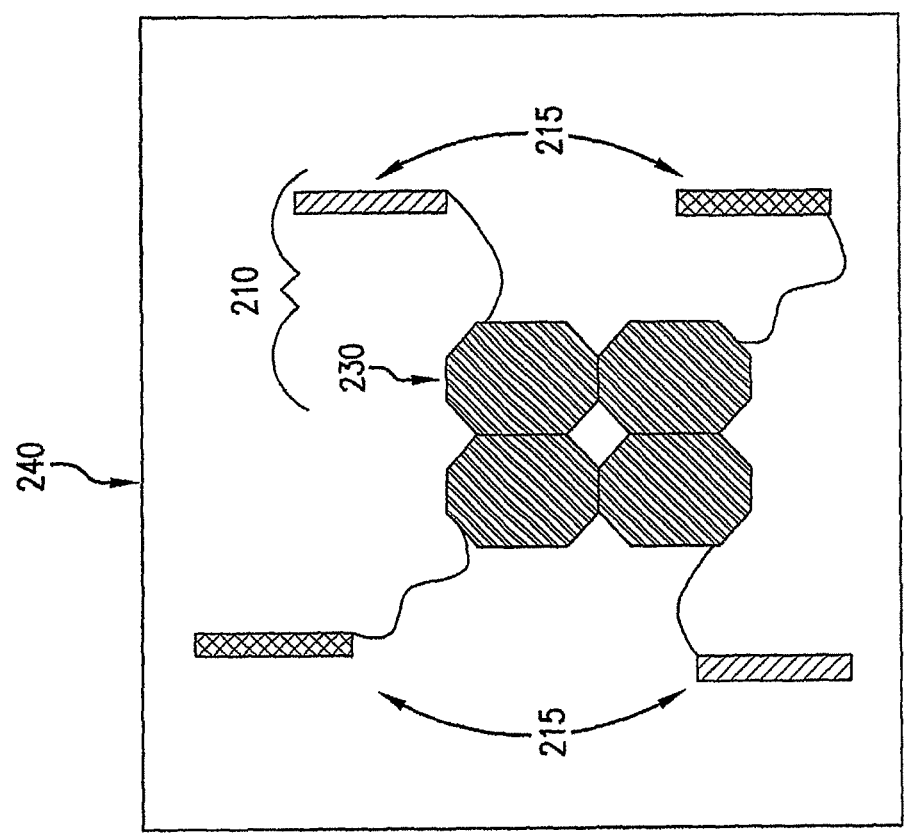
FIG. 2 is a diagram of another protein hydrogel monomer which has formed a tetramer and which incorporates a bio-active protein in accordance with some embodiments of the disclosed subject matter.

Referring to FIG. 2, another embodiment of a protein hydrogel monomer incorporating a bio-active protein is described. In this embodiment, the protein hydrogel monomer 210 is asymmetrical and includes only one helical domain 215. In this embodiment, the bio-active protein 230 interacts with itself to form, for example, a tetramer 240, such that the resulting tetramer contains multiple helices 215, thereby allowing for formation of a hydrogel through interaction of the helical domains.

Figure 3:
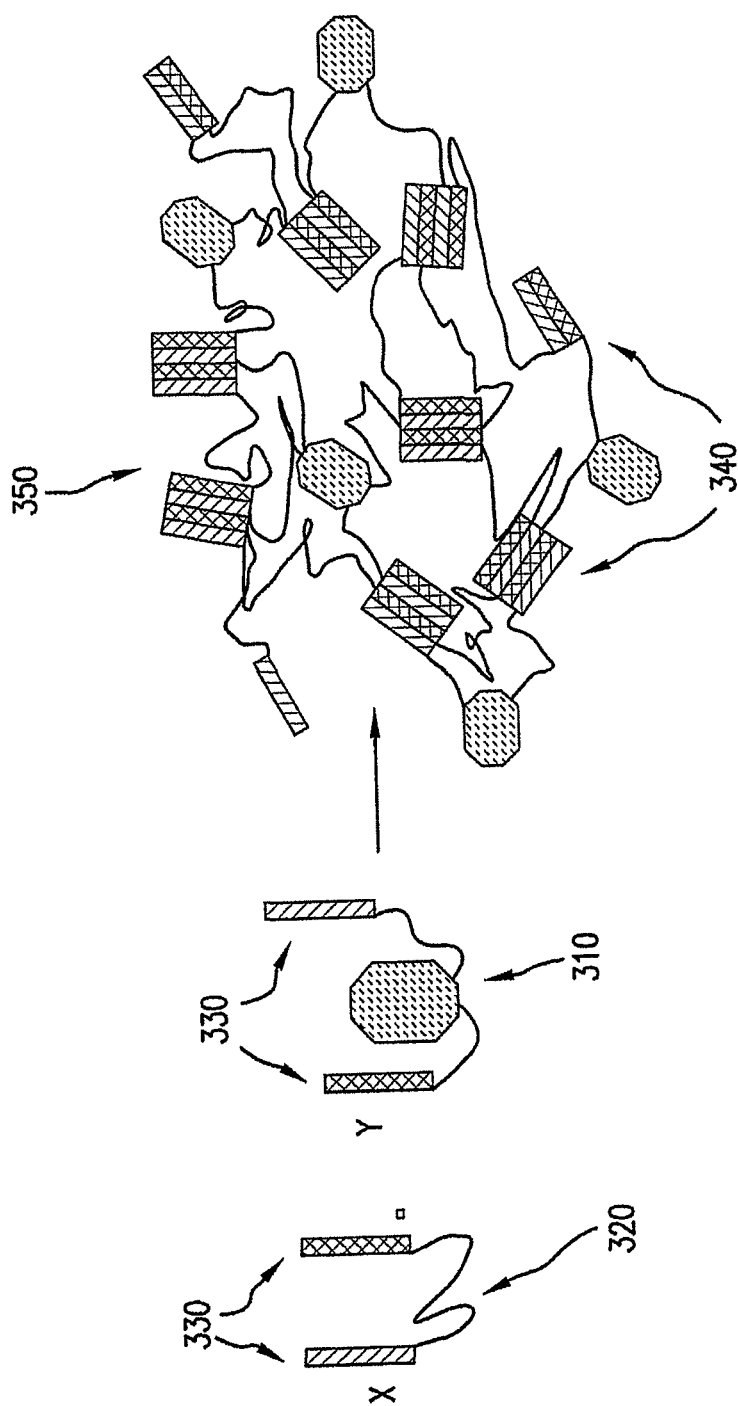
FIG. 3 is a diagram of a protein hydrogel incorporating a bio-active protein including multiple units of the monomer of FIG. 1 and a monomer lacking the bio-active protein in accordance with some embodiments of the disclosed subject matter.

Referring to FIG. 3, a protein hydrogel incorporating a bio-active protein including multiple units of the monomer of FIG. 1 310 and a monomer lacking the bio-active protein 320 is presented. Under the desired environmental conditions, aggregates of the helices 330 of both types of monomers form coiled coil junctions 340 resulting in the formation of a water soluble network of the monomers 350, a protein hydrogel incorporating the bio-active protein. The conditions for gel formation from the monomer depend on the solution characteristics of the bio-active protein. The protein must also not significantly interact with the helical domains, preventing formation of coiled coil junctions or otherwise interfere with gel formation.

In one embodiment, the monomer can be manufactured in one piece using biological manufacturing methods. The production of genetically synthesized materials generally begins with the insertion of a piece of DNA (e.g., chemically synthesized, or isolated, or derived from a natural source) into a circular cloning vector through a series of cutting and ligating reactions. The DNA encodes a specific sequence of amino acids. In this case, the protein monomer can be created through recombinant DNA techniques resulting in the expression of the bio-active protein and hydrogel forming domains as a single protein. Once the DNA sequence is created, it can be inserted into an expression vector or plasmid that allows for protein production in a prokaryotic or eukaryotic host microorganism such as a bacterium (e.g., *E. coli*) or a yeast (e.g., *S. cerevisiae*). The host microorganism is then cultured in a growth medium. After the microorganism has reproduced itself multiple times, the amount depending on the quantity of protein desired, expression of the DNA sequence is stimulated. After allowing the DNA to be expressed for a time, again dependent on the amount of protein desired, the cells are lysed to release the protein, which is extracted and purified.

EXAMPLE 1

GFP-Protein Hydrogel

Figure 4:
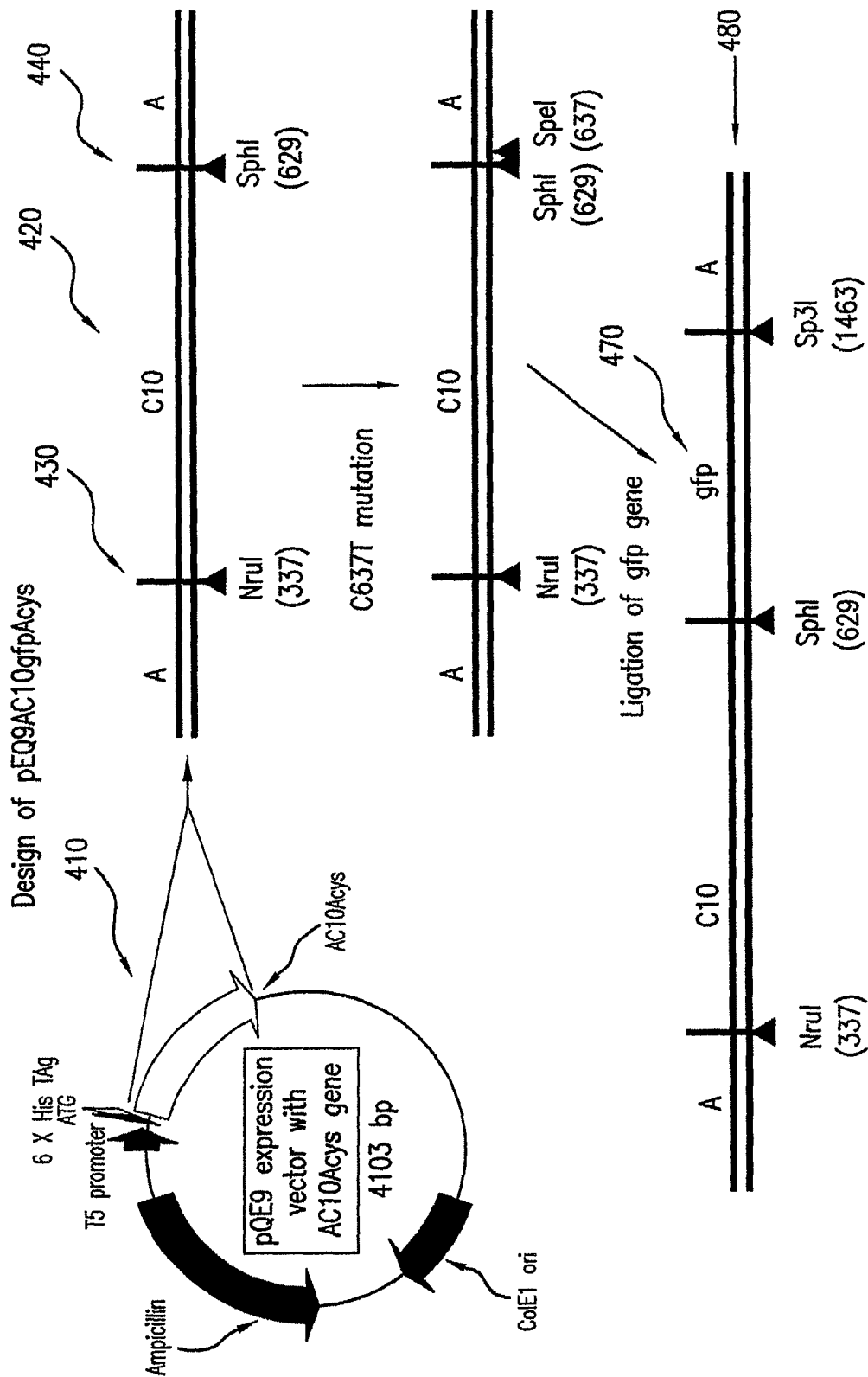
FIG. 4 is a diagram illustrating a method of assembly of an expression plasmid for an asymmetrical monomer including green fluorescent protein (GFP) implemented in accordance with some embodiments of the disclosed subject matter.

Referring to FIG. 4, an exemplary technique for the assembly of the expression plasmid for an asymmetrical monomer including green fluorescent protein (GFP) is described. The process starts with an expression plasmid 410 encoding a protein hydrogel monomer, in this case, the tri-block protein, AC10Acys, described in U.S. Pat. No. 6,090,911. The plasmid is designated as pQE9AC10Acys, where "A" represents the helical heptad repeat and C10 the randomly coiled, soluble region. At the C terminal end of the protein is a single cysteine residue. The portion of the plasmid expressing the prior art protein 420 contains two restriction sites 430 & 440. After digesting the DNA sequence with the appropriate restriction enzymes to cut a restriction site 440, as shown in FIG. 4, the gene for expressing the bio-active protein 470 (in this case, GFP) was ligated into the resulting gap to create the final sequence 480.

Figure 5:
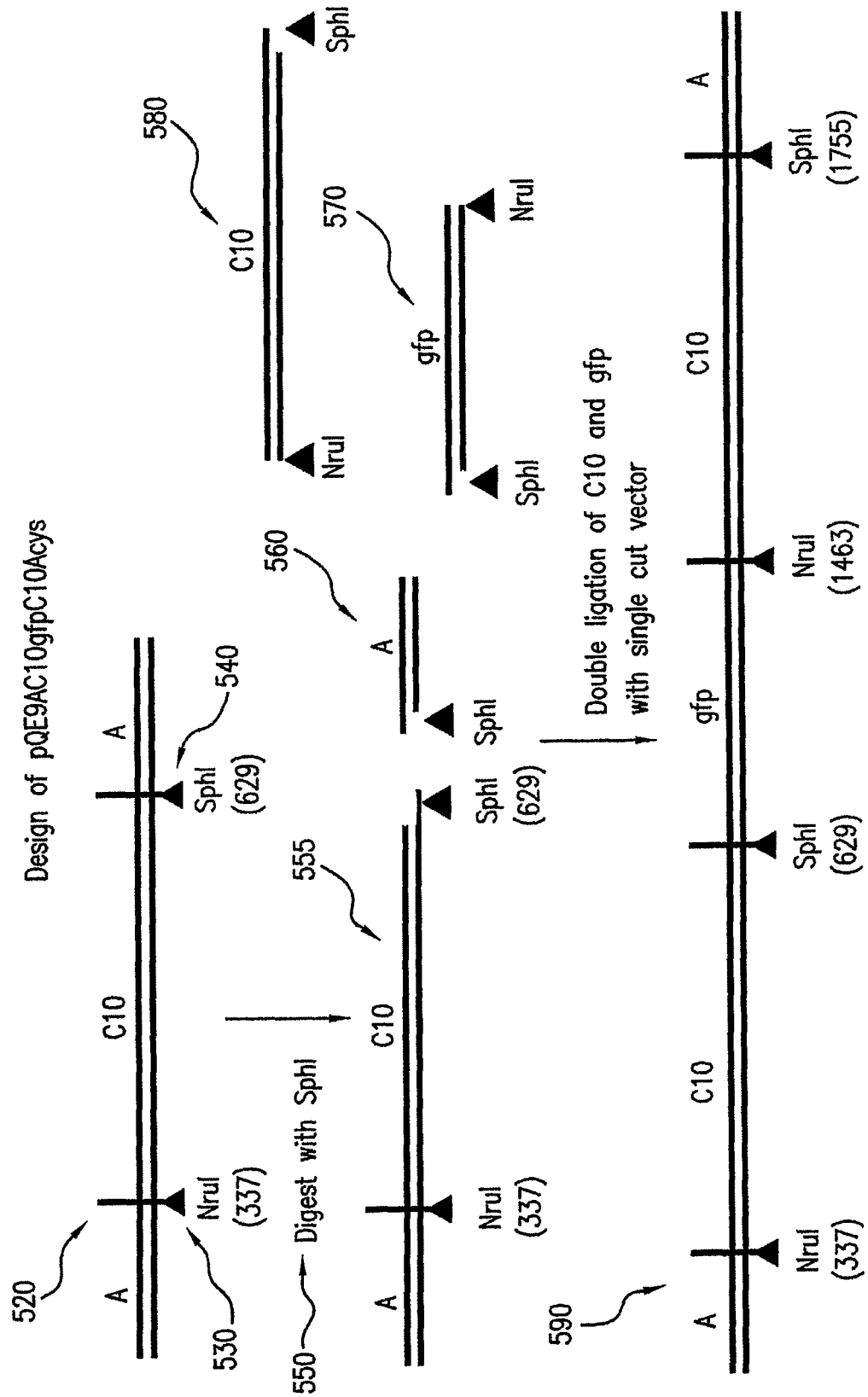
FIG. 5 is a diagram illustrating a method of assembly of an expression plasmid for a symmetrical monomer including green fluorescent protein (GFP) implemented in accordance with some embodiments of the disclosed subject matter.

Referring to FIG. 5, an exemplary technique for the assembly of the expression plasmid for a symmetrical monomer is described. Similar to the plasmid for the asymmetrical monomer, the process starts with an expression plasmid encoding the prior art tri-block protein, AC10Acys. The portion of the plasmid expressing the prior art protein 520 contains two restriction sites 530 & 540. After digestion of the DNA sequence with the appropriate restriction enzyme (SphI) 550, the sequence is split into "AC10" 555 and "A" 560 sections. A double ligation then takes place in which the gene for expressing the GFP protein 570 and a duplicate sequence encoding the randomly coiled region 580 are incorporated into the gap between the AC10 and A sections, creating resulting sequence 590.

Figure 6:
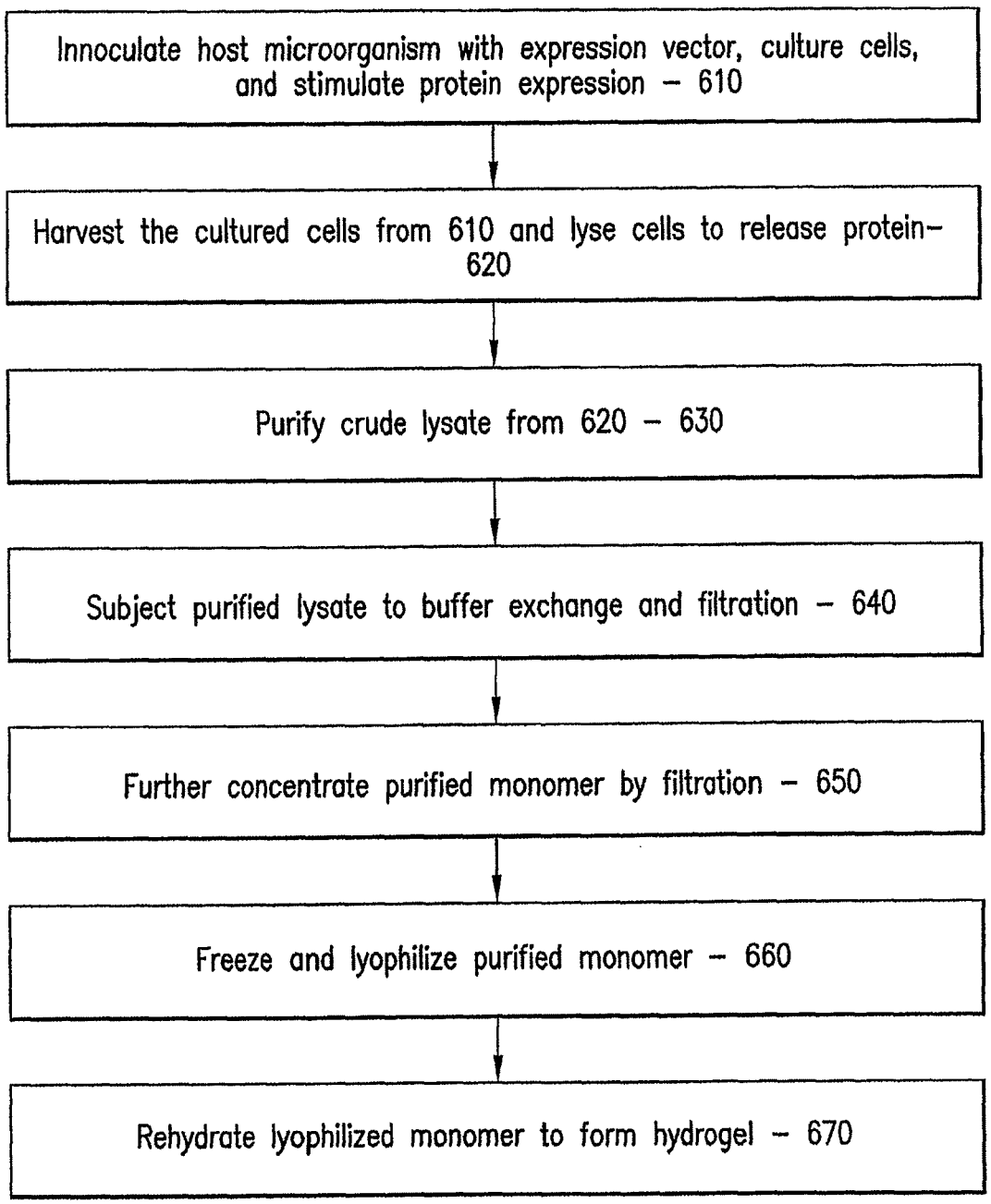
FIG. 6 is a diagram illustrating a method of production of a monomer including a bio-active protein, GFP, and formation of the corresponding hydrogel implemented in accordance with some embodiments of the disclosed subject matter.

Referring next to FIG. 6, an exemplary technique for the production of the monomer and formation of the hydrogel will be described. The protein hydrogel monomer must first be prepared. At 610, innoculated cultures of suitable cells are grown and protein expression stimulated. For example, in example 1, one liter of Terrific Broth ("TB") media (200 μg/ml of ampicillin and 50 μg/ml of kanamycin) are inoculated with 10 ml of a culture of *E. coli* (SG13009 strain, obtained from Qiagen (Valenica, Calif.)) containing pREP4 (used to repress expression of the gene for the monomer until desired) and pQE9AC10gfpAcys or pQE9AC10gfpC10Acys. The inoculated cultures are then grown at 37° C. to a point at which the optical density of the liquid medium at 600 nm ($OD_{600}$) is 1.0. The temperature is then reduced to 20° C. and expression of the gene induced with a 0.5 mM solution of Isopropyl β-D-1-thiogalactopyranoside (IPTG). This expression is allowed to continue for 18 hours.

Although the example for 610 utilized 1 liter of TB media, any volume, up to and including industrial-sized fermentors suitable for *E. coli* can be used as appropriate. Similarly, the amount of culture of *E. coli* used can be from 5 ml to any volume, up to and including volumes required for inoculation of industrial-sized fermenters, and other microorganisms, such as *S. cerevisiae* can be substituted. Luria-Bertani (LB) media can be used instead of TB media, but results in lower yields. Other bacterial cell culture medias such as 2xYT can also be used, but it is preferable to use 'rich' medias such as TB for higher protein yields. Although the culture was grown at 37° C., a temperature range of 20° C. to 37° C. may be used. Similarly, although gene expression was induced when the optical density of the liquid medium at 600 nm reached 1.0, an optical density between 0.85 and 1.05 can be used. Although the temperature was reduced to 20° C. and expression of the gene induced with a 0.5 mM solution of Isopropyl β-D-1-thiogalactopyranoside (IPTG), the expression can be induced with 0.5 mM to 1.5 mM IPTG and conducted at from anywhere between 20° C. to 37° C., and. Finally, although expression was stopped at 18 hours, it can be allowed to continue for 18-20 hours at 20° C., or shortened to 5 hours at 37° C., producing smaller yields.

At 620, the cultured cells are harvested and lysed. For example, in example 1, the cultured *E. coli* cells are harvested, e.g., by centrifugation at 15,000 g for at least 15 minutes. The resulting cell pellets are then re-suspended in 100 ml per liter of culture of nickel affinity chromatography binding buffer (consisting of 20 mM imidazole, 20 mM monobasic sodium phosphate, 20 mM dibasic sodium phosphate, and 500 mM NaCl, at a pH of 7.4). The cells are then lysed by subjection to a freeze thaw cycle to −80° C. and then distrupted by sonication. The resulting lysate can be clarified by centrifugation at 15,000 g for 30 minutes.

Although in the example for 620 the cultured *E. coli* cells were harvested, e.g., by centrifugation at 15,000 g for at least 15 minutes, the centrifugation can be conducted at 5,000-20,000 g for 15-60 minutes as appropriate. Similarly, although the resulting cell pellets are then re-suspended in 100 ml per liter of culture of nickel affinity chromatography binding buffer (consisting of 20 mM imidazole, 20 mM monobasic sodium phosphate, 20 mM dibasic sodium phosphate, and 500 mM NaCl, at a pH of 7.4), the buffer can be composed of 5 to 25 mM of imidazole, 5 to 50 mM total phosphate salt and 300 to 500 mM NaCl, at a pH of 7.2-7.5 and volumes of 10 to 1000 ml can be used. Although the cells were subjected to a freeze thaw cycle to −80° C. and then disrupted by sonication, they can also be lysed by repeated freeze-thaw cycles alone, osmotic pressure, or mechanical force. Finally, although the resulting lysate was clarified by centrifugation at 15,000 g for 30 minutes, the centrifugation can be conducted at 10,000-20,000 g for 15-30 minutes as appropriate.

At 630, the monomer is purified from the crude lysate. For example, in example 1, the crude lysate is purified, e.g., with a Fast-Liquid-Low-Pressure Chromatography system (ÄKTA 900, available from GE Healthcare, Uppsala, Sweden, a unit of General Electric Co.) equipped with a nickel affinity column (HisTrap™ Crude, 5 ml, also available from GE Healthcare). For example, in example 1, 50 ml of crude lysate is injected into the column and washed with 40 ml of the previously-described binding buffer. The resulting bound protein is eluted with 20 ml of elution buffer (consisting of 375 mM imidazole, 20 mM monobasic sodium phosphate, 20 mM dibasic sodium phosphate, and 500 mM NaCl, at a pH of 7.4), and has a high imidazole salt concentration.

Although in 630 the monomer was purified from the crude lysate using an ÄKTA 900 Fast-Liquid-Low-Pressure (FLLP) Chromatography system equipped with a 5 ml His-Trap™ Crude nickel affinity column, the momomer can also be purified using weak anion exchange chromatography. Columns such as the HiPrep™ 16/10 DEAE FF (GE Healthcare) are suitable for purification with a low-salt binding buffer with a pH above the isoelectric point (pI) of the monomer and eluted with a high-salt concentration eluent or an eluent at a pH below the pI of the monomer. If a FLLP Chromatography system is used, any nickel affinity column can be used. If a HisTrap™ Crude, 5 ml nickel affinity column is used, the binding buffer may be composed of 5 to 20 mM of monobasic sodium phosphate, 5 to 20 mM of dibasic sodium phosphate, 0.3 to 0.5 mM NaCl and 0 to 25 mM sodium imidazole, with a pH range of 7.2-7.5, while the elution buffer is similar, except that the imidazole ranges from 250 to 1000 mM.

Similarly, while 50 ml of crude lysate was injected into the column, the amount of lysate that can be injected into the column is limited only by the maximum capacity of the column. Larger volumes of more dilute lysate solution or smaller volumes of a higher concentration can also be injected. More specifically, 1 to 50 ml of lysate produced using the method of example 1 can be injected, and anywhere from 0.1 to 1000 ml of lysate of the appropriate concentration can be injected. Bound monomer can be washed with 5 to 1000 ml of the previously-described binding buffer. Although the resulting bound protein was eluted with 20 ml of elution buffer, 5-50 ml can be used.

At 640, fractions containing the monomer are pooled and subjected to buffer exchange and filtration. For example, in the case of a GFP-hydrogel monomer, green-colored fractions are those containing the monomer, while in the case of a RFP-hydrogel, red-colored fractions are those containing the monomer. Similarly, colors relating to chromophores present in other bio-active proteins may be used to identify fractions containing their respective monomers. In the case of an enzyme that lacks a chromophore, the absorbance at 280 nm can be used to identify fractions containing high protein concentrations. In example 1, e.g., buffer exchange to 3.4 mM monobasic sodium phosphate and 16.6 dibasic sodium phosphate is then conducted over a 30 kDa cellulose filter, commercially available from Millipore Corp. (Billerica, Mass.). The buffer exchange and filtration removes high levels of salts resultant from the purification and proteins with a molecular weight less than ~30 kDA.

Although in the example for 640 the buffer exchange was conducted to 3.4 mM monobasic sodium phosphate and 16.6 dibasic sodium phosphate, the buffer exchange can be conducted to 1-50 mM monobasic and 1-50 mM dibasic.

At 650, purified monomer is further concentrated by centrifugation. For example, in example 1, centrifugation is conducted over a 10 kDA cellulose filter (Centriplus, commercially available from Millipore Corp.). The resulting concentrated solutions of protein are aliquoted into 1.5 ml microcentrifuge tubes, although clear 96 well UV plates or black 384 well plates, both available from Corning, Inc. (Lowell, Mass.) can be used.

At 660, the samples are frozen and lyophilized. For example, in example 1, the samples are then frozen to −20° C. and lyophilized, e.g., using a FreeZone 1 freeze dry system, commercially available from Labconco Corp. (Kansas City, Mo.). Solutions at higher concentrations, such as those greater than about 25 mg/ml, are incubated at −80° C. for one hour prior to lyophilizaiton to ensure complete freezing. The resulting powder contains the purified monomer. Although in the example for 660 the samples were incubated at −80° C. for one hour, they can be incubated at −40° C. to −80° C. for one to eight hours.

At 670, the hydrogel is formed by re-hydration of the powder. For example, in example 1, the powder is re-hydrated with de-gassed H$_2$O and/or 100 mM phosphate buffer (mono- and dibasic) at pH 7.5 to a concentration of approximately 15 wt % monomer with a 7 mM concentration of helices. Since the lyophilized powder contains some buffer, the gel may be formed by either the addition of the de-gassed H$_2$O, 100 mM phosphate buffer at pH 7.5, or a combination of the two. Dissolution of the lyophilized protein can be aided by vortexing and mechanical mixing when required. Air bubbles are removed from the hydrogel samples after mixing by centrifugation for 1 minute at 10,000 g. In an embodiment utilizing microtiter plates, no vortexing or mixing takes place, rather the samples are centrifuged at 2,000 rpm for 5 minutes after rehydration.

Although in the example for 670, the hydrogel is formed by re-hydration of the powder to a concentration of approximately 15 wt % monomer with a 7 mM concentration of helices, concentrations as low as 9.7 wt % monomer and 4 mM helices are possible. Similarly, concentrations of up to 49 wt % GFP-hydrogel monomer and 53 wt % DsRed-monomer have been observed. Although 100 mM phosphate buffer was used, concentrations between 50 and 200 mM can be used. GFP-hydrogels can be formed with between 1 and 10 M methanol in aqueous 100 mM phosphate buffer. Other salt pairs that buffer within a pH range of 5 to 9 can be used for hydrogel formation. Although hydrogel formation has been shown at temperatures between 4 and 60° C., the optimal temperature is application dependent; for example, the optimal temperature for enzymatic hydrogels must balance enzymatic activity, enzymatic stability, and hydrogel stability.

Figure 7:
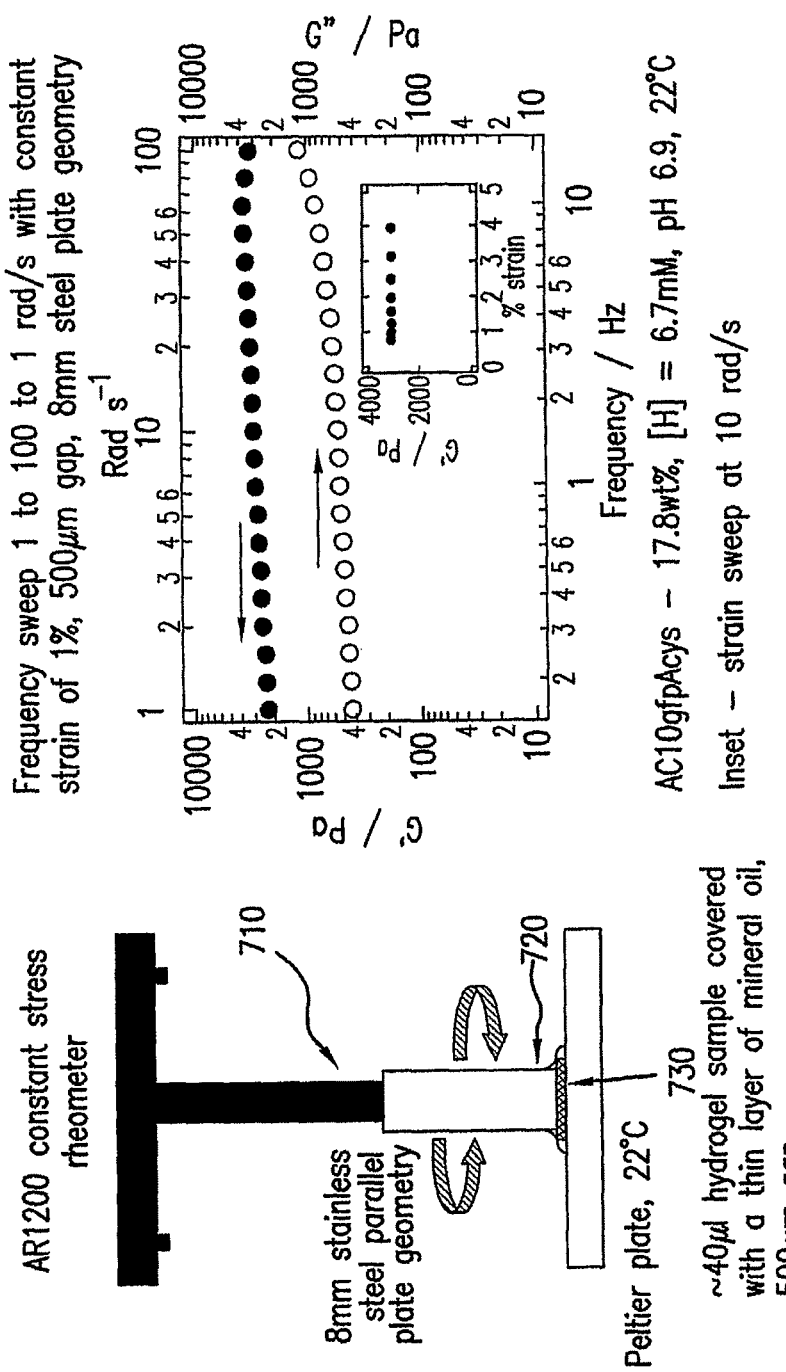
FIG. 7 is a diagram illustrating a rheological analysis of a GFP hydrogel produced using the method of FIG. 6 in accordance with some embodiments of the disclosed subject matter.

Referring next to FIG. 7, rheological analysis of the resulting GFP hydrogel will be described. Using a constant stress rheometer 710 with an 8 mm stainless steel parallel plate 720 geometry, and a 500 μm gap, a ~40 μl hydrogel sample 730 was analyzed. A frequency sweep from 1 to 100 to 1 rad/s with a constant strain of 1% was conducted. As evidenced by the plot, the results showed a stable and high storage modulus, indicating a stable hydrogel was formed.

Figure 8:
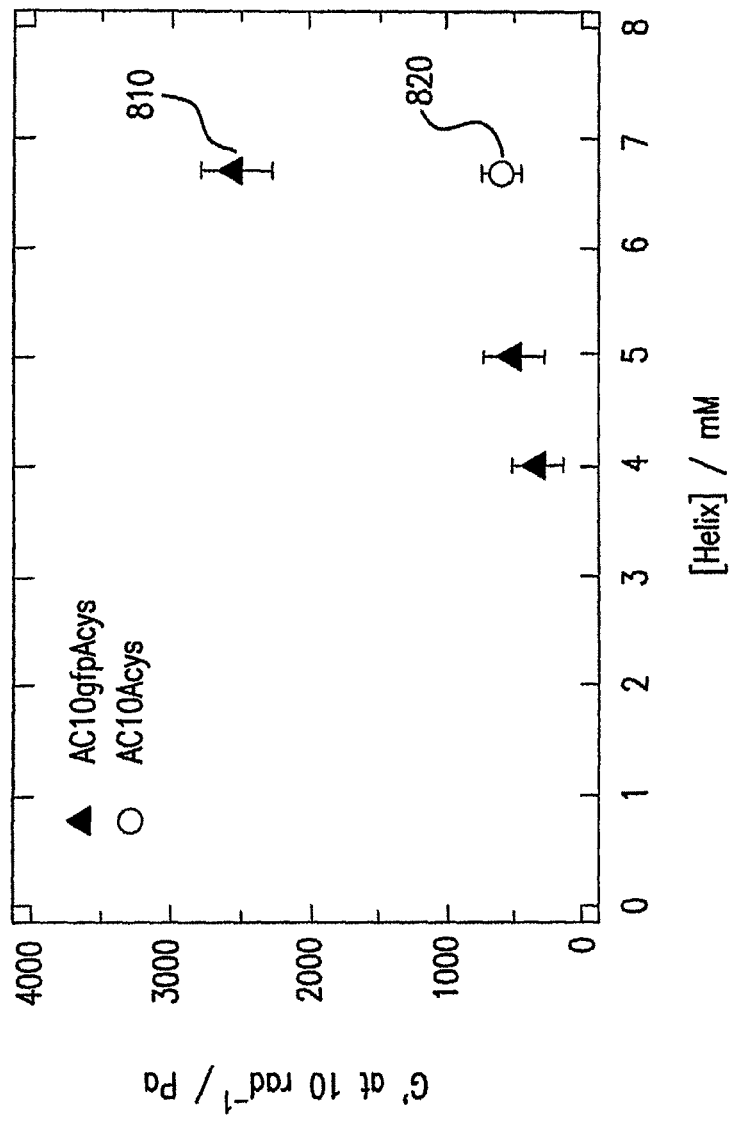
FIG. 8 is a comparison of the relative hydrogel strength (as measured by storage modulus) of a hydrogel formed of the prior-art monomer versus a hydrogel formed of the GFP monomer produced in accordance with some embodiments of the disclosed subject matter.

Referring next to FIG. 8, a comparison of the relative hydrogel strength (as measured by storage modulus) of a hydrogel formed of the prior-art monomer versus a hydrogel formed of the GFP monomer is described. The test was conducted using the same equipment as described previously, at a setting of 10 rad/s, at 22° C. in 100 mM phosphate buffer. At the same density of helical regions the strength of the GFP monomer 810 is much greater than that of the prior-art monomer 820.

Figure 9:
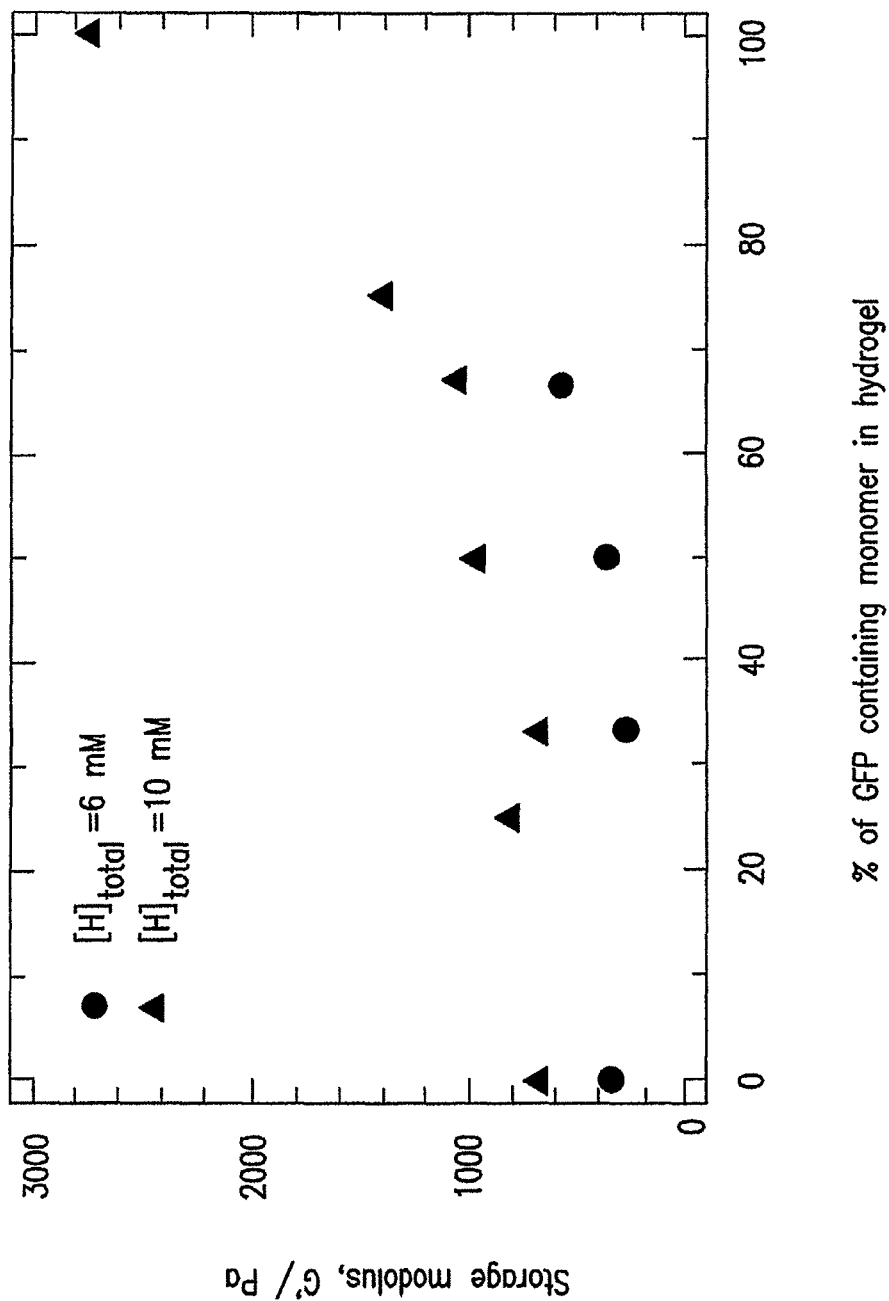
FIG. 9 is a comparison of the relative strength of a series of hydrogels containing increasing proportions of GFP-monomer at two different densities of helical regions produced in accordance with some embodiments of the disclosed subject matter.

Referring next to FIG. 9, the relative strength of a series of hydrogels containing increasing proportions of GFP-monomer at two different densities of helical regions is described. As the percentage of GFP containing monomer in the hydrogel increases, the relative strength of the hydrogel increases. From this it can be seen that addition of a bio-active protein to an existing monomer actually strengthens the hydrogel formed by the monomer. Thus, a novel self-assembling peptide hydrogel can be formed that contains the green fluorescent protein (GFP). Rheometry data shows that the new material spontaneously forms a stable hydrogel (as evidenced by a stable and high storage modulus), and fluorescence images show that the GFP chromophore is functional. By mixing the GFP containing hydrogel monomer with the prior art monomer, the GFP content of the gels can be precisely tuned at a constant helical content ([H]=6 mM or 10 mM).

Referring next to FIG. 10A, a plot of the fraction of hydrogel released versus time for a hydrogel formed from the prior art monomer 1010 and for a hydrogel formed from the GFP monomer 1020 is shown. The fraction of hydrogel released from the prior art hydrogel is much greater than that of the GFP hydrogel, showing that the GFP hydrogel degrades slower and lasts longer than the prior art hydrogel.

Referring next to FIG. 10B, a plot of the amount of fluorescence in open buffer (as opposed to in the hydrogel) versus time are shown for a hydrogel formed from a mixture of the prior art monomer and unmodified GFP 1030 and a hydrogel formed from the GFP monomer 1040. After two hours, there is much more free-floating florescence in the hydrogel formed from the mixture 1030, than in that formed from the GFP monomer 1040, indicating that, when expressed as a single protein, the GFP stays in the hydrogel longer and does not leach out of the hydrogel as fast as that of a simple mixture (most likely due to the fact that the GFP is covalently bonded to the helical domains of the hydrogel). The tests of both FIG. 10A and FIG. 10B were conducted at 26° C. with an open buffer solution 25× hydrogel volume.

Figure 11:
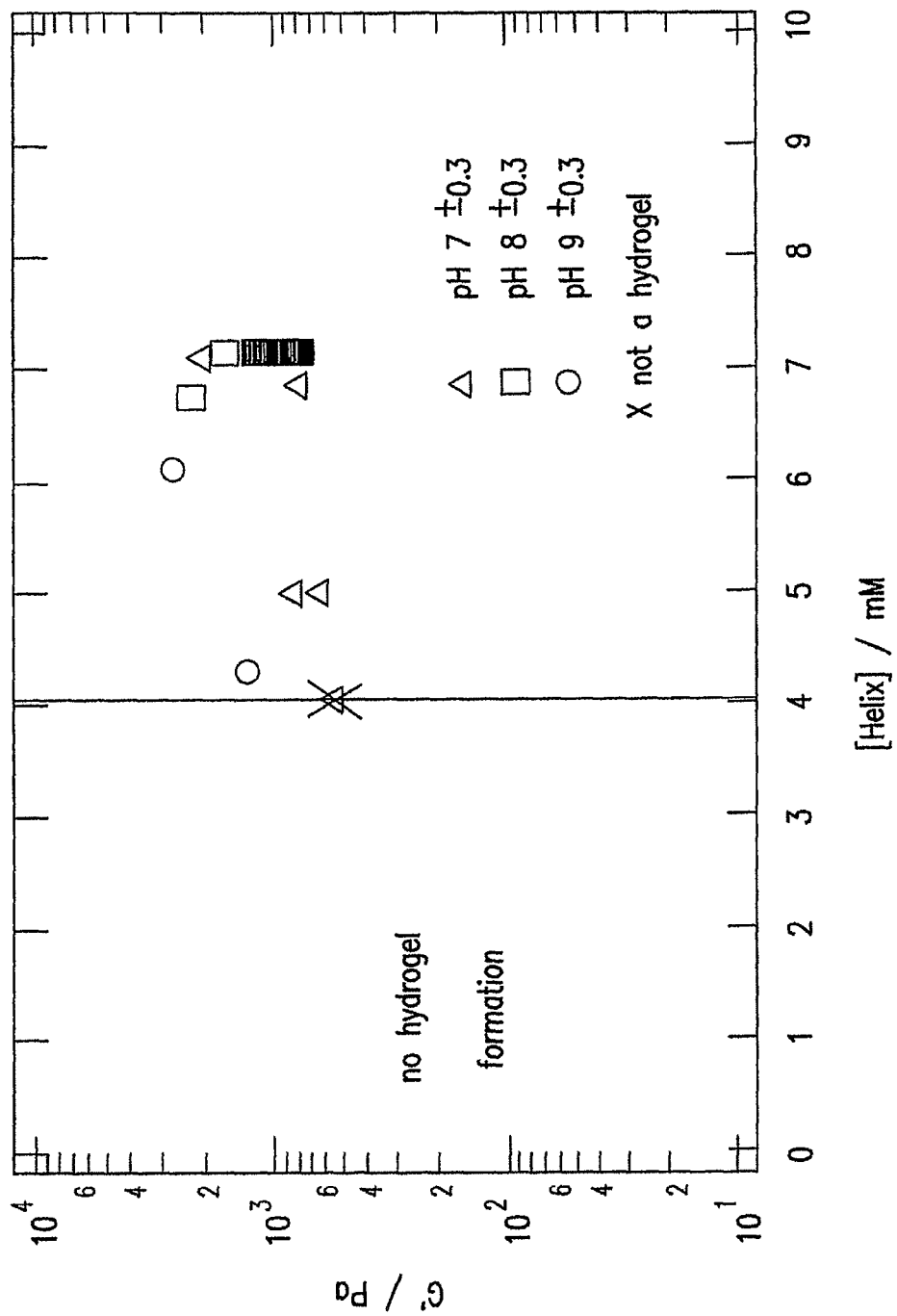
FIG. 11 is a plot of the storage modulus versus helix concentration for GFP-monomer hydrogel samples at various pH values.

Referring next to FIG. 11, a plot of the storage modulus versus helix concentration for GFP-monomer hydrogel samples at various pH values is shown. Hydrogel formation was not observed below a concentration of 4 mM helices and 9.7 wt % monomer.

Figure 12:
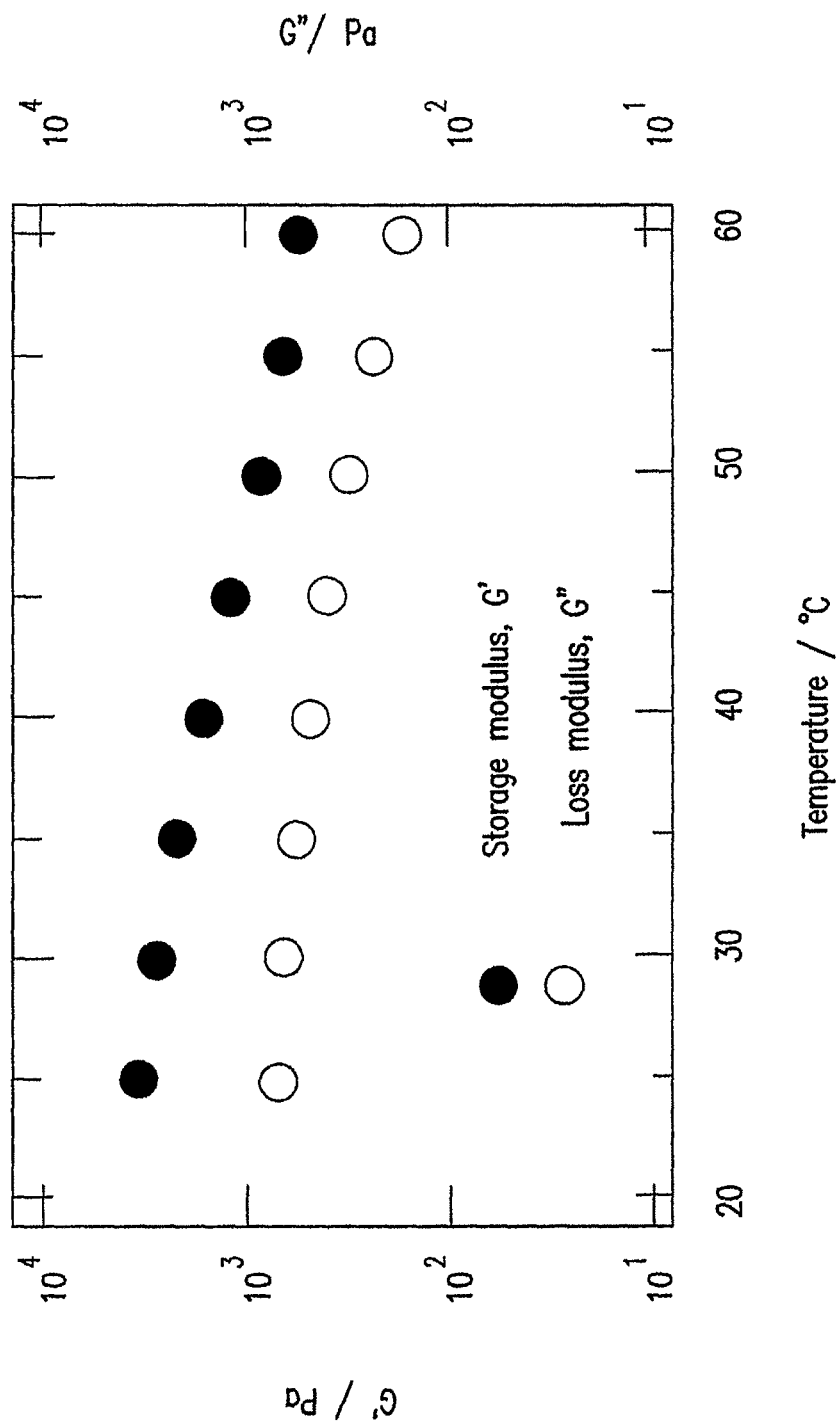
FIG. 12 is a plot of the storage and loss modulus of a GFP-monomer hydrogel sample at various temperatures.

Referring next to FIG. 12, a plot of the storage and loss modulus of a GFP-monomer hydrogel sample at various temperatures is shown. The storage modulus of the sample decreases with temperature, indicating a loss in elastic character, but the sample still demonstrates hydrogel behavior.

EXAMPLE 2

DsRed-Protein Hydrogel

An exemplary technique for the assembly of hydrogel with only one terminal helix using DsRed red fluorescent protein as the bio-active protein instead of GFP will now be described. The DsRed monomer can react with itself to form a tetramer containing four DsRed proteins and four terminal helices. The expression sequence was created using the same techniques as that used for creating the sequence for expression of the GFP monomer, although the sequence contains only one "A" domain, resulting in a sequence of AC10DsReds.

The plasmid encoding the monomer, pQE9AC10dsred, was constructed in a similar fashion as pQE9AC10gfpA as previously described. The gene encoding DsRed was excised from pCMV-DsRed-Express, available from Clontech Laboratories, Inc. (Mountain View, Calif.). The gene was then ligated into pQE9AC10Acys at the unique SphI and SpeI sites. Using the same method as that described for formation of the GFP monomer, the sequence was placed in *E. coli*, which was then cultured. Expression of the sequence was stimulated using ITPG, and time allowed for the protein to be produced. The cells were then lysed and the protein purified using the previously-described techniques.

Figure 13:
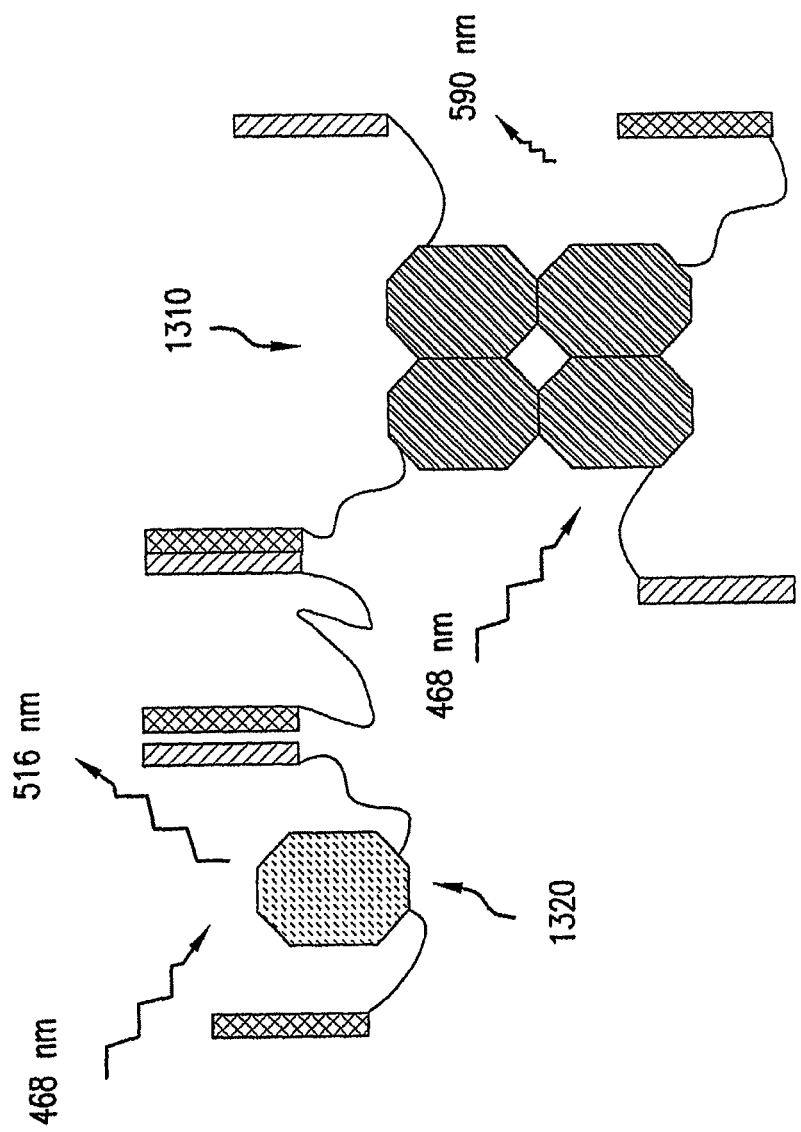
FIG. 13 is a diagram of a protein hydrogel monomer incorporating both a DsRed monomer and GFP monomer, produced in accordance with some embodiments of the disclosed subject matter.

Referring next to FIG. 13, the DsRed tetramer can form a hydrogel in the same manner as the GFP monomer, and a hydrogel can, in fact, be formed from a mixture of DsRed monomer 1310 and GFP monomer 1320. The resulting fluorescent hydrogel will fluoresce at the frequencies of both GFP and DsRed, producing a mixed color.

Concentrated solutions of DsRed-hydrogel monomer were lyophilized and re-hydrated to form a hydrogel using the same process as that described previously for the GFP-hydrogel. The DsRed monomer forms a novel hydrogel in which the cross-linking within the hydrogel is in part due to multimer formation and in part due to the aggregation of alpha-helices into coiled coils, as in the GFP hydrogel.

Figure 14:
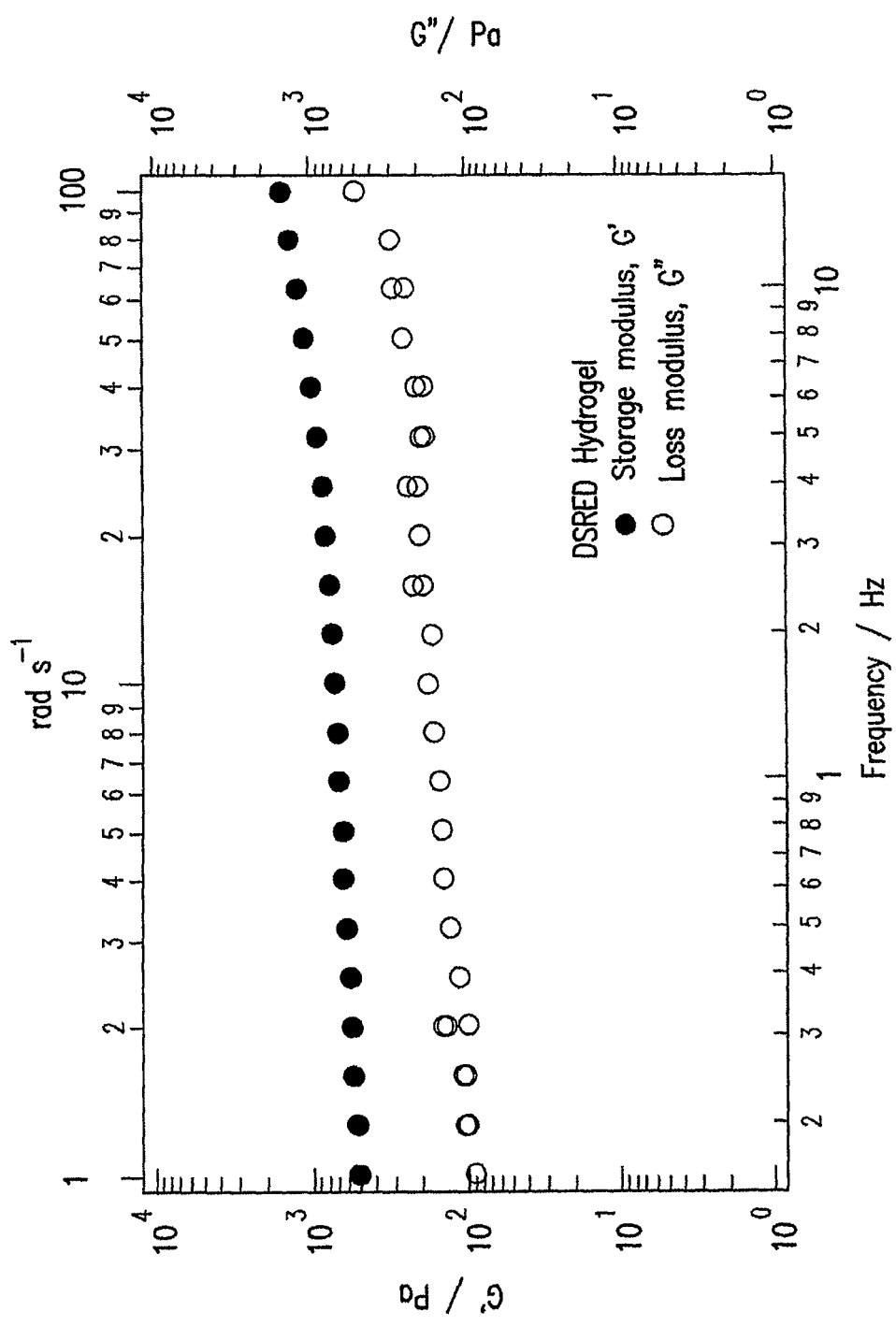
FIG. 14 is a diagram illustrating a rheological analysis of a DsRed hydrogel produced using the method of FIG. 6 in accordance with some embodiments of the disclosed subject matter.
Figure 15:
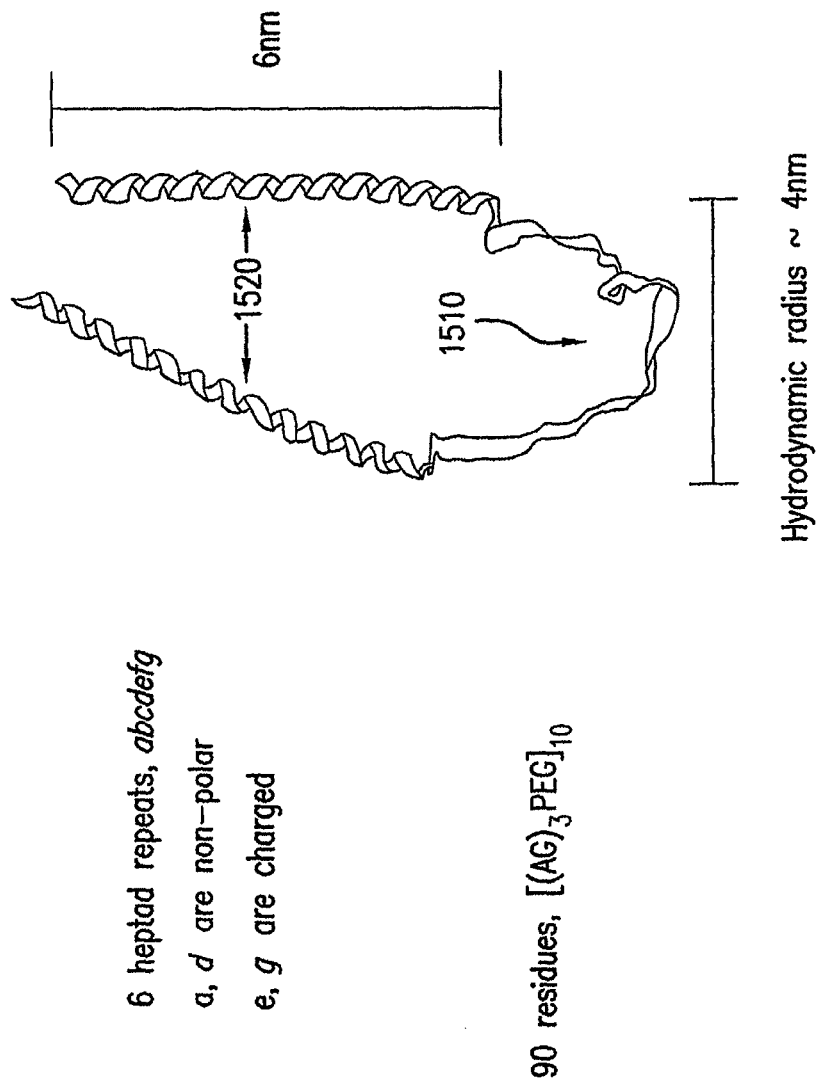
FIG. 15 is a diagram of a prior-art protein hydrogel monomer.
Figure 16:
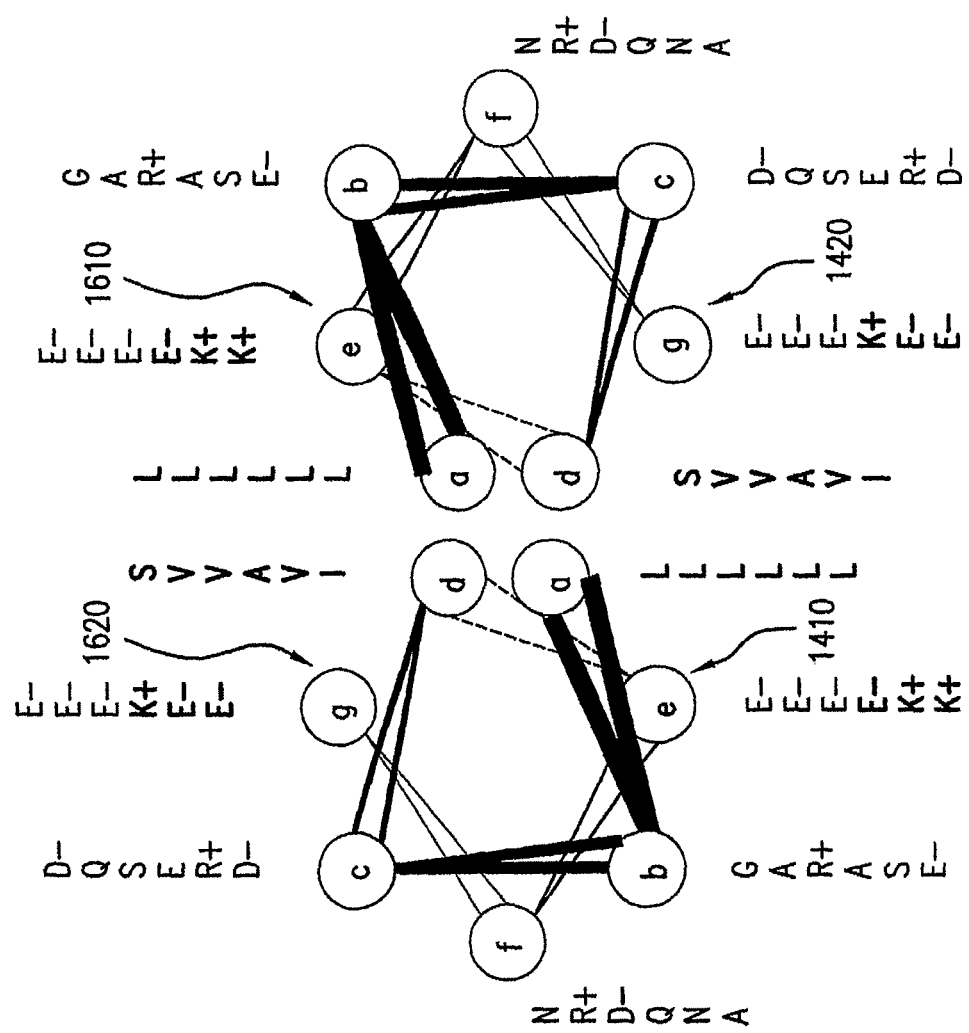
FIG. 16 is a diagram of the angular orientation of the helical residues in the prior-art protein hydrogel monomer of FIG. 15.

Referring next to FIG. 14, rheological analysis of the resulting DsRed hydrogel will be described. Using a constant stress rheometer with an 8 mm stainless steel parallel plate geometry, and a 500 μm gap, a ~40 μl hydrogel sample was analyzed. A frequency sweep from 1 to 100 to 1 rad/s with a constant strain of 1% was conducted. The storage modulus and loss modulus for a 21.1 wt % DsRed hydrogel sample is shown. As evidenced by the plot, the average storage modulus between 1 and 50 rad/s was 330 Pa, a factor of 3 greater than the loss modulus over the same frequency range, thus indicating a stable hydrogel was formed.

EXAMPLE 3

Enzymatic Protein Hydrogel

An exemplary technique for the assembly of an enzymatic protein hydrogel will now be described. The enzyme is SLAC, a small laccase which includes four copper ions and is active against a range of substrates, preferring to bind against those that are negatively charged. (See Machczynski, M. C.; Vijgenboom, E.; Samyn, B.; Canters, G. W., Characterization of SLAC: A small laccase from *Streptomyces coelicolor* with unprecedented activity. *Protein Sci.* 2004, 13, 2388-2397). A plasmid, pQE9AC10slacAcys, encoding the enzymatic protein hydrogel was constructed in a similar fashion as the previously described plasmid pQE9AC10gfpA encoding the GFP protein hydrogel. The gene sequence for SLAC is publicly available (accession number CAB4558), and can be exised from the genome of *Streptomyces coelicolor* (See Machczynski et al. above).

The protein was expressed and purified as follows. One liter of TB media was innoculated with 10 ml of a culture of SG13009 expression line *E. coli* (Qiagen) were grown to an $OD_{600}$ of 1.5 at 30° C. The temperature was then reduced to 25° C. and expression of the gene and induced with 0.4 mM IPTG. Overexpression of the protein continued for 20 hrs.

The cells were harvested by centrifugation at 15,000 g for 15 minutes. The resulting cell pellets were resuspended in 100 ml of 10 mM phosphate buffer pH 7.3. The cells were then disrupted by sonication. The resulting crude lysate was incubated with 1 mM $CuSO_4$ for 3 hours at room temperature. The now copper-containing lysate was dialyzed 4 times against 2 L of 10 mM phosphate buffer pH 7.3 for 8-10 hours. 1 mM EDTA was added to the second dialysis solution as a chelating agent to remove any unbound copper.

The dialyzed crude lysate was purified by nickel affinity chromatography as previously described with respect to purification of the GFP protein. The resulting eluted fractions containing the desired protein were concentrated over a 30 kDa cellulose filter and the buffer was exchanged to 20 mM phosphate, pH 7.5.

The activity of small laccase modified with hydrogel forming domains as determined by colorimeteric assay with N,N-dimethyl-1,4-phenylenediamine (dmpdau) or dimethoxyphenol (DMP) as co-substrate will now be described. Assays were conducted in a 250 µl volume buffered to pH 7.0 with 100 mM phosphate with 50 mM DMP or 10 mM dmpda. The consumption of DMP and dmpda was monitored by measuring the absorbance of the assay solution at 468 and 550 nm respectively. Table 1 summarizes the activity of the AC10slacAcys samples with saturating concentrations of dmpda and DMP at 25° C. Activity is stated in terms of µmol of co-substrate and oxygen per min per mg of protein sample.

TABLE 1

| Sample | $Cu^{2+}$/mM | mg protein | substrate | Specific activity µmol min$^{-1}$mg$^{-1}$ | +/− | Specific activity O2 µmol min$^{-1}$mg$^{-1}$ | +/− |
|---|---|---|---|---|---|---|---|
| AC10slacA | 0.0 | 0.017 | DMP | 0.004 | 1E−04 | 0.001 | 3E−05 |
| AC10slacA | 1.0 | 0.017 | DMP | 0.018 | 0.007 | 0.005 | 0.002 |
| AC10slacA | 0.1 | 0.083 | DMP | 0.030 | 0.010 | 0.008 | 0.002 |
| AC10slacA | 0.0 | 0.017 | dmpda | 2.373 | 0.089 | 0.593 | 0.022 |

That the protein exhibits activity demonstrates that the fusion of the hydrogel forming tails to both the N- and C-terminals did not significantly disturb the $Cu^{2+}$ binding sites or the catalytic active sites of the small laccase. The increase in activity with the addition of $Cu^{2+}$ ions to the assay solution suggests that some bound copper may have dissociated overtime or during protein purification.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention.

The invention claimed is:

1. A protein hydrogel monomer having the formula:

A-C-B-C-D, wherein
   A and D are protein blocks, each including an alpha-helical region adapted to self-assemble with an alpha-helical region of A or D blocks on other protein hydrogel monomers to form a coiled-coil;
   C is a water-soluble random coil block; and
   B is a bio-active protein having a globular three dimensional structure in solution; wherein the monomer is capable of forming hydrogel.

2. The protein hydrogel monomer of claim 1, wherein A and D are non-identical.

3. The protein hydrogel monomer of claim 1, wherein A and D are identical.

4. The protein hydrogel monomer of claim 1, wherein B is GFP.

5. The protein hydrogel monomer of claim 1, wherein B is an enzyme.

6. A protein hydrogel monomer having the formula:

A-C-B-D, wherein
   A and D are protein blocks, each including an alpha-helical region adapted to self-assemble with an alpha-helical region of A or D blocks on other protein hydrogel monomers to form a coiled-coil;
   C is a water-soluble random coil block; and
   B is a bio-active protein having a globular three dimensional structure in solution, wherein the monomer is capable of forming hydrogel.

7. The protein hydrogel monomer of claim 6, wherein A and D are non-identical.

8. The protein hydrogel monomer of claim 6, wherein A and D are identical.

9. The protein hydrogel monomer of claim 6, wherein B is GFP.

10. The protein hydrogel monomer of claim 6, wherein B is an enzyme.

11. A protein hydrogel monomer having the formula:

A-C-B wherein
    A is a protein block including an alpha-helical region adapted to self-assemble with an alpha-helical region of a terminal protein block on other protein hydrogel monomers to form a coiled-coil;
    C is a water-soluble random coil block; and
    B is a bio-active protein having a globular three dimensional structure in solution, wherein the monomer is capable of forming hydrogel.

12. The protein hydrogel monomer of claim 11, wherein the structure of B is adapted to self-assemble with the bio-active protein regions on one or more other protein hydrogel monomers to form a multimer.

13. The protein hydrogel monomer of claim 11, wherein B is DsRed.

14. The protein hydrogel monomer of claim 11, wherein B is an enzyme.

15. A method of preparing a protein hydrogel monomer incorporating a bio-active protein, wherein the protein hydrogel monomer is a protein hydrogel monomer of claim 1, claim 6, or claim 11, the method comprising:
   a) inserting an expression vector containing hydrogel-forming and bio-active protein domains into a host microorganism, the expression vector adapted to cause the expression of the hydrogel-forming and bio-active protein domains as a single protein hydrogel monomer incorporating a bio-active protein;
   b) culturing the host microorganism in a growth medium;
   c) stimulating expression of the expression vector;
   d) lysing the cells to release the monomer; and
   e) purifying the monomer from the lysate.

16. The method of claim 15 wherein the host microorganism is *E. coli*.

17. The method of claim 15 wherein the expression vector is a plasmid pQE9AC10XAcys, where X is the bio-active protein.

18. The method of claim 15 wherein the expression vector is a plasmid pQE9AC10XC10Acys, where X is the bio-active protein.

19. The method of claim 15 wherein purifying the monomer from the lysate further comprises:
   f) treating the lysate using nickel affinity chromatography to produce an eluent;
   g) conducting buffer exchange on the eluent;
   h) filtering the buffered eluent.

20. The protein hydrogel monomer of claim 1, wherein the self-assembly of the A or D blocks on the protein hydrogel monomer with the A or D blocks on other protein hydrogel monomers are by way of at least one of hydrophobic interactions, and charge-charge interactions.

* * * * *